United States Patent [19]

Valenti

[11] Patent Number: 5,584,795
[45] Date of Patent: Dec. 17, 1996

[54] PIVOTING LARYNGOSCOPE HAVING A POWER-DRIVEN CURVED SPATULA

[76] Inventor: Elio Valenti, Via del Loretino, 17, I-50135 Firenze, Italy

[21] Appl. No.: 244,814

[22] PCT Filed: Dec. 12, 1992

[86] PCT No.: PCT/IT92/00161

§ 371 Date: Dec. 6, 1994

§ 102(e) Date: Dec. 6, 1994

[87] PCT Pub. No.: WO93/11700

PCT Pub. Date: Jun. 24, 1993

[30] Foreign Application Priority Data

Dec. 13, 1991 [IT] Italy ................................. FI91A0296

[51] Int. Cl.⁶ ..................................................... A61B 1/267
[52] U.S. Cl. .......................... 600/196; 600/197; 600/198
[58] Field of Search .................................. 600/109, 118, 600/146, 190, 194, 197, 199

[56] References Cited

U.S. PATENT DOCUMENTS 1,568,732  1/1926  Haslinger .
4,314,551  2/1982  Kadell ................................. 600/197
4,360,008  11/1982  Corazzelli, Jr. .
4,384,570  5/1983  Roberts .
4,556,052  12/1985  Müller ................................. 600/199
4,941,456  7/1990  Wood et al. ............................ 128/6

Primary Examiner—Richard J. Apley
Assistant Examiner—Kelly McGlashen
Attorney, Agent, or Firm—Spencer & Frank

[57] ABSTRACT

A pivoting laryngoscope has a power-driven spatula for performing intubation in patients. The laryngoscope includes a handle for gripping the laryngoscope, and a curved spatula blade having one end connected to the handle. The spatula blade is subdivided into a plurality of adjacent, sequentially arranged sections. At least two of the sections are pivotally connected together at a fulcrum. A motorization assembly is located within the handle and is activatable for generating movement. A motion transmission assembly operatively connects the motorization assembly to at least one of the sections for transmitting the movement of the motorization assembly to the section, whereby the section is moved relative to the fulcrum and within a predetermined arc, thereby changing a curvature of the curved spatula blade.

19 Claims, 5 Drawing Sheets

PIVOTING LARYNGOSCOPE HAVING A POWER-DRIVEN CURVED SPATULA

BACKGROUND OF THE INVENTION

The present invention concerns a surgical instrument, specifically a pivoting laryngoscope having a power-driven, curved spatula, used for performing intubation of patients under anesthesia or in resuscitation.

As it is known, before performing surgery, it is necessary to anesthesize the patient. Anesthesia is obtained through drugs which work to completely suspend pain sensitivity in a temporary and reversible way. The anesthetic effect, generally obtained by using alcaloid drugs and muscle relaxants, affects the brain, the cerebellum, the spinal cord and the peripheral nervous system in general, and is furthermore accompanied by a paralysis of the respiratory centers, variable only in intensity and duration exclusively through the use of different drugs.

It is well known that prolonged paralysis of respiratory centers, causes brain damage and, in cases where the duration of the drugs' effect has extended itself beyond a given amount of time, death from asphyxia.

In surgical practice, when the patient undergoes anesthesia, artificial respiration is given by means of external machinery specifically designed for this purpose, after having connected the patient to the same through cannulae and tubes. Connecting the patient to the machine requires a significant amount of manual maneuvers, generally executed by the anesthesiologist, which in medical practice are known as "intubation", consisting of the introduction of a tube or cannula through the mouth, the larynx and trachea to the lungs, the tube being then connected to tee respiratory machinery.

In order to understand the problem, it must be taken into account that the above-described maneuver must be executed with means and within a time frame defined by the progressive paralyzing effect upon the respiratory centers generally brought about through alcaloid anesthetics and muscle relaxants or other similar drugs. Therefore, the duration of the intubation process cannot extend itself beyond a generally brief and definite time frame, also because of the mechanical difficulties inherent to the introduction of the cannula of tube.

Usually, in order to execute the intubation maneuver, the anesthesiologist uses a mechanical instrument, typically a spatula-tube mounted at a right angle on a handle, of the same type as that which is used to execute laryngoscopies, bronchioscopies or esophagoscopies. The instrument having been introduced in the patient's mouth, the anesthesiologist reaches, by means of the spatula, the base of the toungue and the laryngeal wall of the epiglottis and with a quick pivoting movement straightens the spatula-tube into an almost vertical position, and then, with small, slow motions, introduces the cannula along the laryngeal cavity.

The manner of execution of this maneuver, as traditionally executed and with the known instruments, presents some inconveniences.

First of all, it must be noted that the maneuver needs to be executed by pivotally moving the cannula-guiding instrument, in order that the lowering of the toungue and the dental arch allows the cannula to travel along the medial line of the trachea in an axis as direct as possible to the point of introduction, that is, the mouth.

Such a pivoting movement, is obviously not obtainable by using an instrument having the cannula-guiding spatula placed at a right angle to the handle. Similarly a curved spatula does not resolve the problem since such a curve, being permanently set, could not be adapted to the multiple positions which are produced by the rotation of the head and the neck in various situations.

The intubation maneuver operator frequently operates on patients having acquired pathologies, such as cervical arthrosis or mandibular anchylosis, or having congenital deformities such as macroglossis (overdevelopment of the toungue) or "bull neck", which make it extremely difficult, if not impossible, to introduce an intubation cannula guided by an instrument which depends on its being pivoted only through the rotation of the patient's head. Such rotation is limited or impeded in the aforementioned cases.

Another inconvenience is that during the introduction of the cannula, the anesthesiologist does not have means for seeing inside the larynx and generally along the entire path which the cannula travels.

SUMMARY OF THE INVENTION

In view of what is said above, this invention has been made with the purpose of allowing intubation of a patient before surgery, regardless of the shape of the patient's neck and toungue, or despite the presence of pathologies which impede complete movement of the head and neck. It is significant that, in order to achieve complete success of the anesthetizing action and, as a consequence, the possibility of connecting the patient to external machinery for artificial respiration or for other purposes, by means of the instrument which is the object of this invention, the introduction of the cannula is greatly facilitated and sped-up, giving the possibility of adapting the cannula guiding instrument to the shape of the involved anatomic parts of the patient.

An additional purpose is to include in the instrument means for an illuminated laryngoscopy during the intubation maneuvers.

These and further purposes are achieved by the invention, by means of a pivoting laryngoscope having a power-driven curved spatula, particularly useful for performing intubation of patients under anesthesia or in resuscitation, characterized by the following:

- a grip-handle for holding, which houses the power means, operating means and power feeding means, as well as motion transmitting parts that transmit power from the power means to a curved spatula connected to them, constituting their performing extension.
- a curved spatula part, typically flattened, subdivided into a number of adjacent sections, the last of which having at one end a circular section ending, and which sections receive movement from the motion transmitting parts present in the handle, which allow the spatula part to be moveable in a radial direction, with respect to a fulcrum, defined within a pre-determined arc.

BRIEF DESCRIPTION OF THE DRAWINGS

To achieve a better understanding of the present invention, a description of the preferred embodiment follows, it being understood that it is purely for the purpose of exemplification and is non-limitative to the invention, with reference to the enclosed drawings, in which.

DETAILED DESCRIPTION OF THE INVENTION

Figure 2:
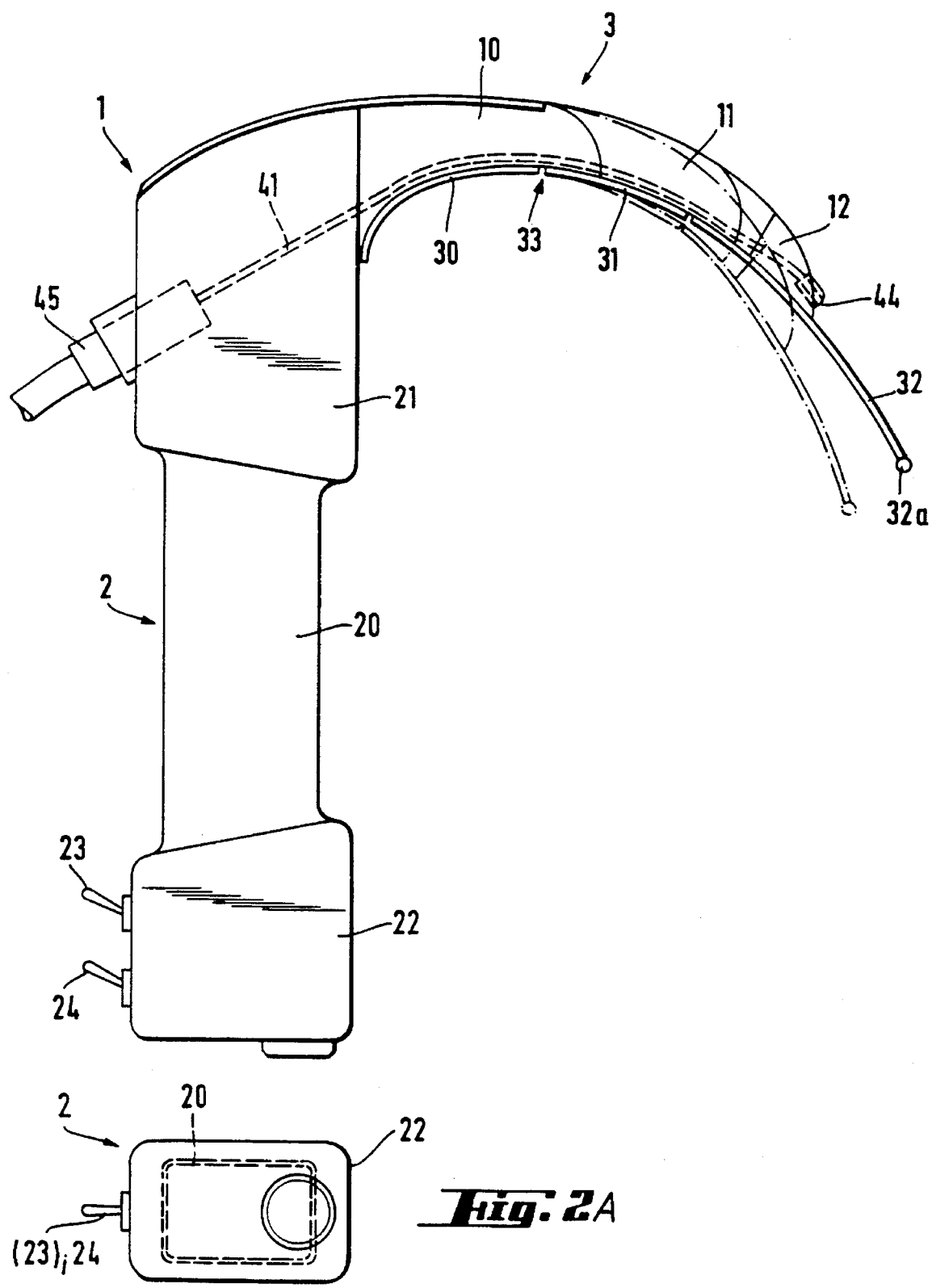
FIG. 2, is a lateral perspective of the laryngoscope indicating the movement of the spatula part and the outline of the path of the sheaf of optical fibers.
Figure 3:
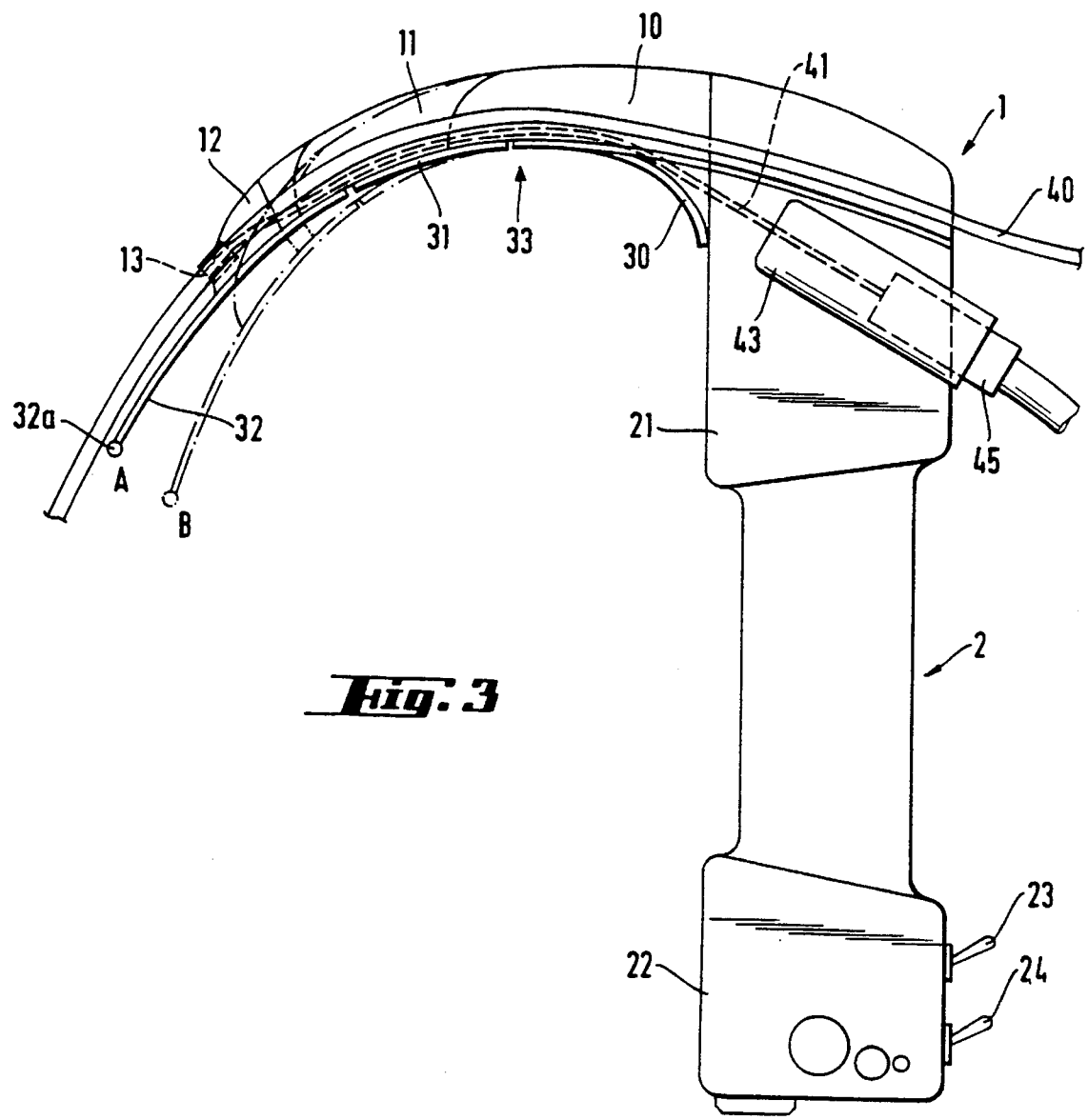
FIG. 3, is a lateral perspective of the laryngoscope as viewed from the side opposite that described above.
Figure 4:
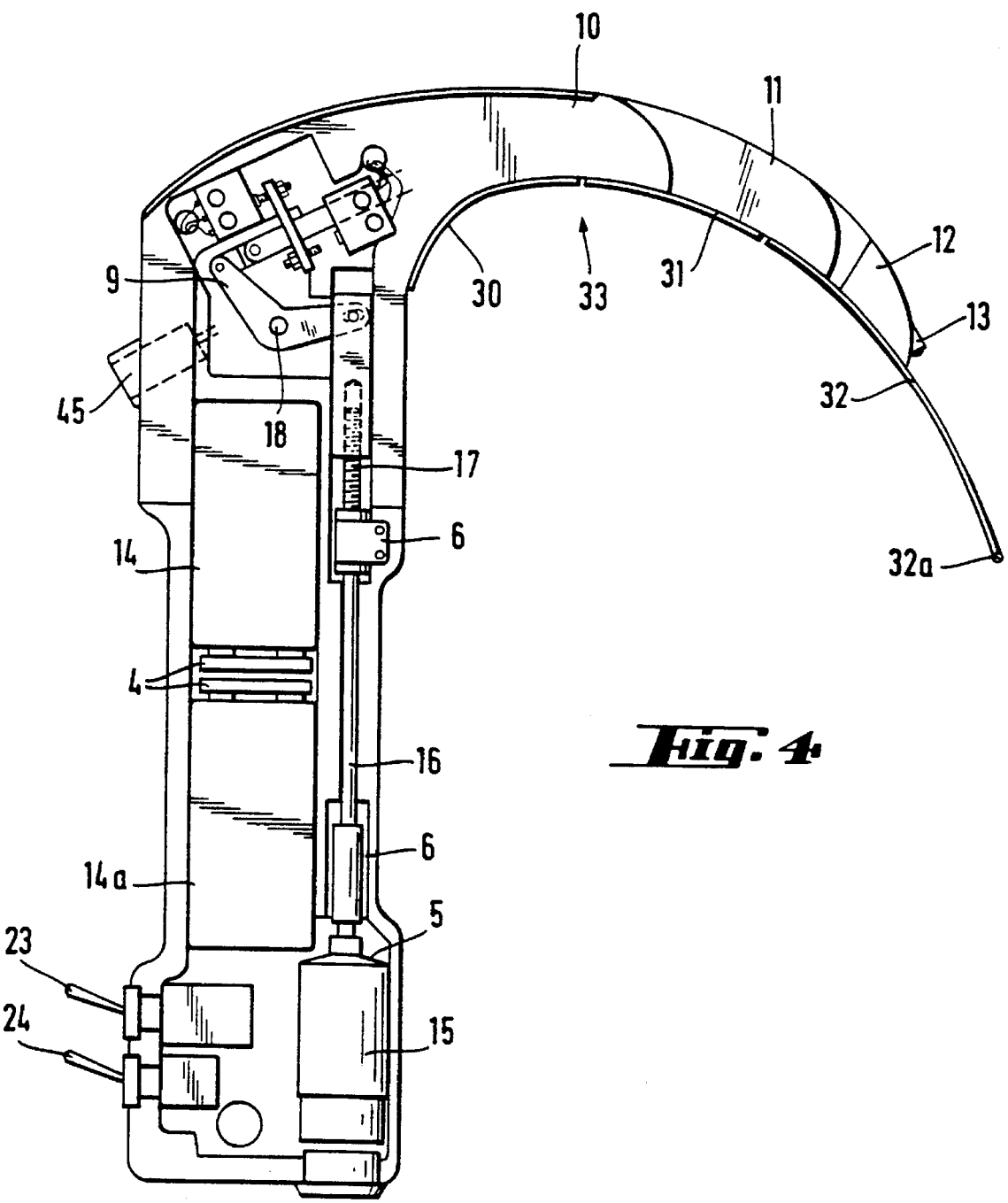
FIG. 4, is a view of the laryngoscope in which the handle part is open to allow viewing of the internal members.

Referring in particular to FIGS. 2, 3 and 4, it is therein indicated in its whole a pivoting laryngoscope 1 with a curved motorized spatula, specifically for performing intubation in patients under anesthesia or in resuscitation.

The device essentially comprises a hollow handle, in its whole indicated with 2, and having a substantially rectangular section 2A, presenting a central portion 20, serving permits holding of the laryngoscope, an inferior ending with a larger section portion 22 and a superior ending with another portion 21 symetrical to 22, from which departs a power-driven curved spatula part 3. The power means 5 of the curved spatula part 3, are housed inside the bottom portion 22 of the handle 2, and, in the embodiment shown as an example, consist of a small electric motor 15 fed by a direct current using two rechargeable batteries 14 and 14A, present in the central portion 20, in the inferior portion 22. In a position opposite that of the small motor 15, the operating means 23 and 24 of the same are found.

From the group of power means 5, through the central portion 20 of the handle part 2, transmission means generically indicated with 6 transmit the movement to a curved spatula part 3, which is connected and dependent upon the superior portion 21, of which it constitutes a performing extention.

The curved spatula 3, typically flattened, is subdivided into a number of adjacent sections 30, 31, 32 each respectively consisting of a curved blade. The adjacent sections carry the performing organs (parts) of the rotation, respectively indicated by 11, 12, 13. The performing organs receive motion from the power means 5, through the group of transmission means 6 present in the handle part 2. The combined rotation (pivoting) of sections 30, 31, 32 determines a progressive pivoting of the blade portions, so as to enact a radial mobility, with respect to a fulcrum 33, which allows the entire spatula part 3 to be variably positioned at different angles and, simultaneously, allows the ensemble of blade sections 30, 31, 32 to take on an adjustable and reversible curvature which is predetermined within the extreme positions A and B.

More specifically, the handle part 2, in its hollow inferior part 22, houses the power means 5, to which is connected one end of a small transmission shaft 16, having at its opposite end a screw segment 17, which in turn has a projection 36 inside a tubular tang 8, having a lead screw. This assembly is moveable, and connects the group of motion transmission organs 6 to the three blade sections 30, 31, 32. The small transmission shaft 16, placed inside the central part 20 of the handle part 2, in conjunction with the power-feeding means (4), during operation causes the tubular tang 8, located in the superior portion 21 of the handle part 20, as it travels, to activate the motion of the transmission organs as the tang 8 moves from position C to C'. The transmission organs consist of an elbow plate 9, having a fulcrum 18, and being hinged on the tubular tang A4 37, and on a shaft 19 at 35. The shaft 19 is in turn hinged at 38 to a second extension shaft 29, and the second extension shaft 29" is hinged on it's opposite end at 39 with the performing part 13. Thus, the transmission organs impart the entire apparatus described above with movement in the direction 34, and to performing parts 11 and 12, which are directly connected to the blade sections 31 and 32 of the spatula part 3.

Figure 5:
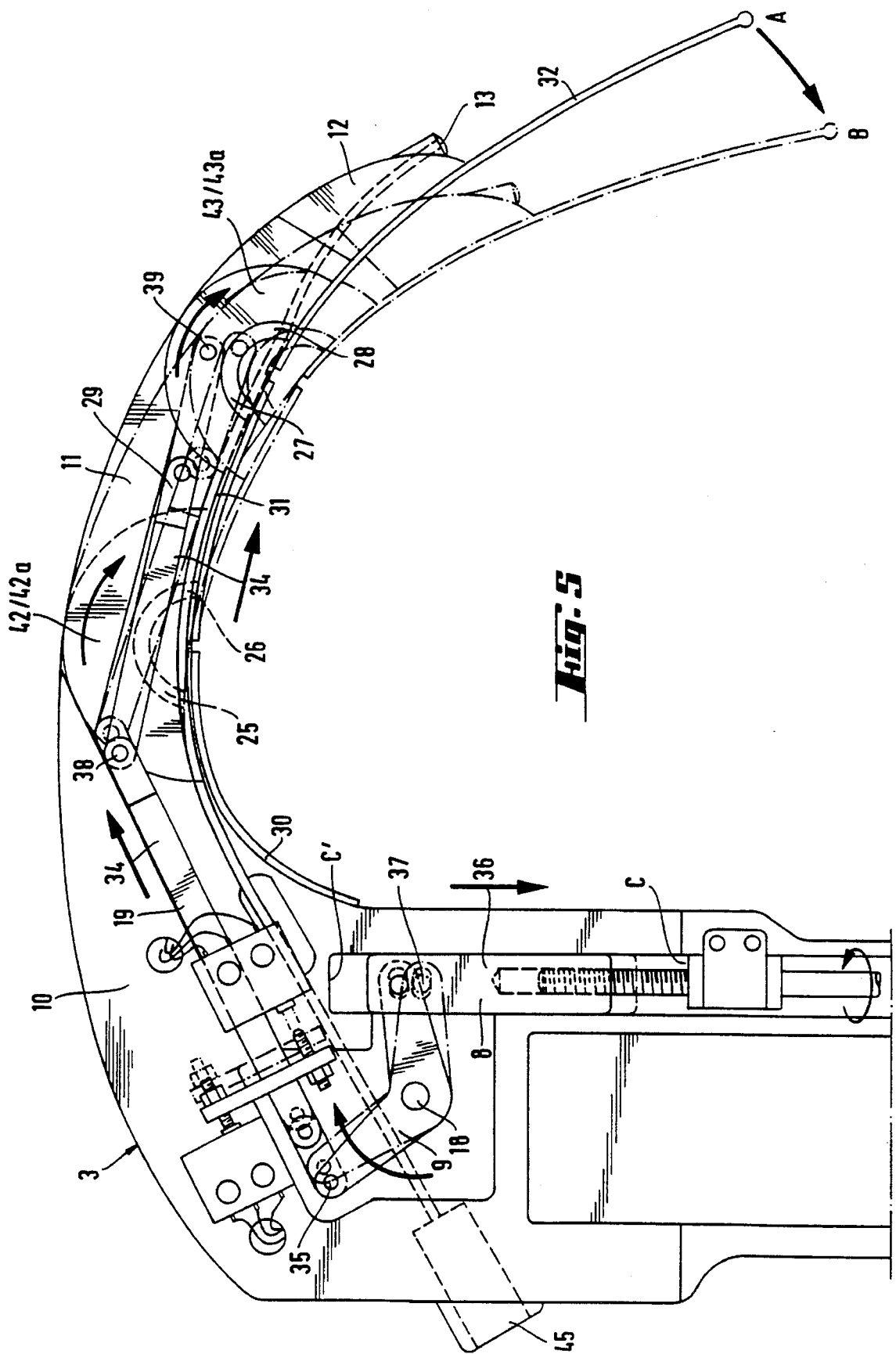
FIG. 5, is a detailed view of the open spatula part.

Referring in particular to FIG. 5, it is noted that elements 10, 11 and 12, which are integral parts of adjacent sections 30, 31 and 32 of spatula part 3, are additionally comprised of two pairs of plates 42/42a and 43/43a. The plates have a semicircular shape, and each respectively has a radial ring-shaped groove 25 and 27 and a radial ring-shaped ledge 26 and 28, which perfectly fit in each other and, in use, rotate upon each other, thereby allowing the respective adjacent sections 31 and 32 of the spatula part ot take on various positions contained within the arc A-B. Thus, the pivoting of the spatula part group can be, varied with the group having its fulcrum at point 33, without needing to adjust the curvature of the spatula, unless the operator desires to do so.

Element 12, placed upon blade section 32, has a terminal end in which are present illumination means 13 consisting of one or more illuminated elements of a known type. The illumination means is activated through a switch 23 found in the inferior potion of the handle 2, and is fed by rechargeable batteries 14 and 14a. Openings 44 of a channel 41 are located in the terminal end. Channel 41 carries a system of optical fibers for transmitting analog or numerical signals, substantially to achieve, by means of a pilot circuit not depicted in the drawing, the emission of corresponding optical impulses to be transformed into electrical signals which can then be amplified, equalized and decoded.

In one variation of the construction, a semiconductor laser, sheaf of a known type can be inserted through the channel 41, into which it is entered through a special housing 43, by employing a special type of connection plug 45. The laser sheaf can be led through the channel to one or more exit openings 44 of element 13. Another alternative which employs the above-described arrangement, could allow for the use of semiconductor devices which use spontaneous emission of the type known as luminous diodes or LED—Light Emitting Diodes.

Figure 1:
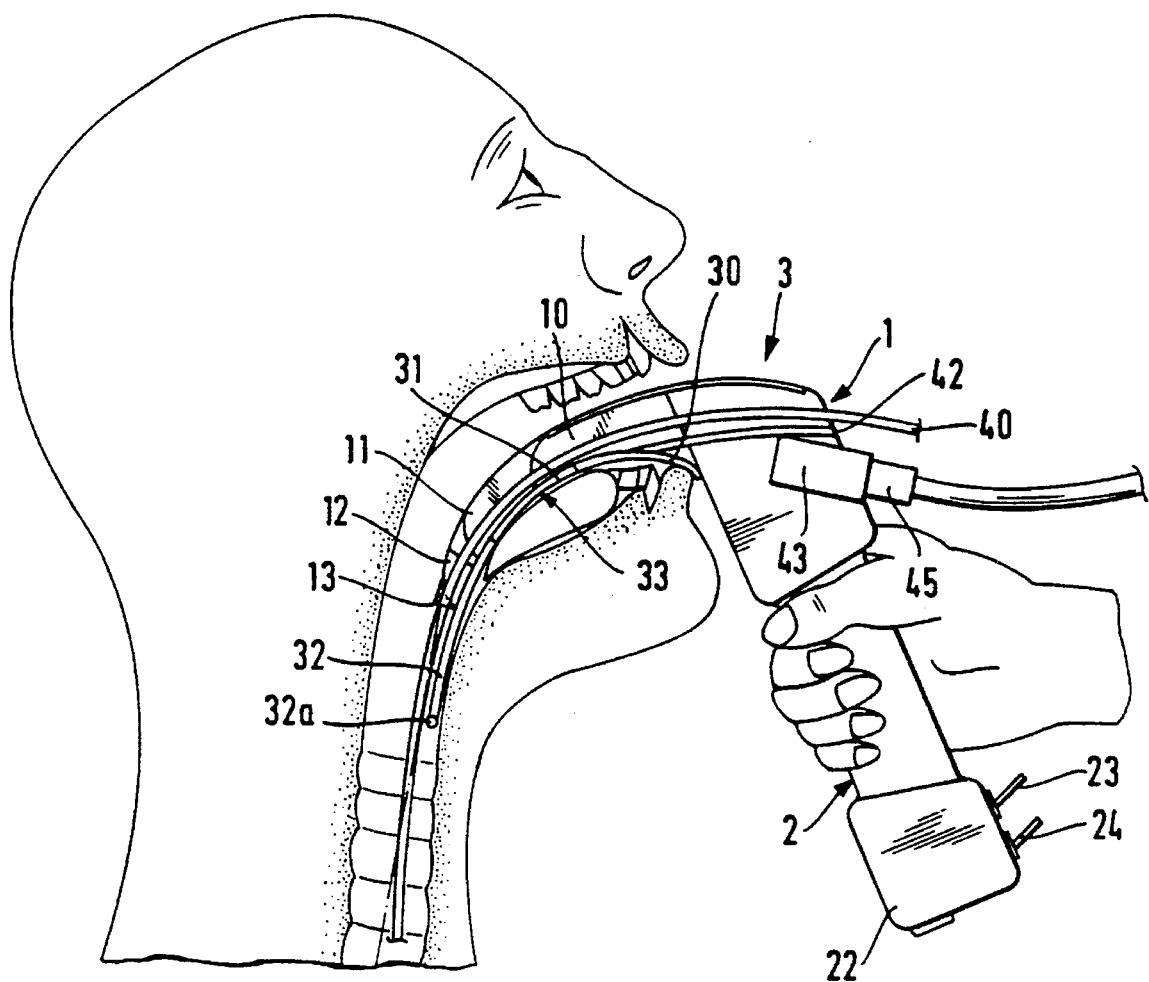
FIG. 1, shows a schematic view of the laryngoscope in an operating position.

The laryngoscope which is the object of the invention as described above, during use (see FIG. 1), allows the user, for example and generically, an anesthesiologist, once he is holding the instrument by section 20 of handle 2, to introduce the spatula blade 3 in the patient's mouth, to reach the base of the toungue and the laryngeal plate of the epiglottis and to progressively adapt the position of the spatula blade 3 through the motorized pivoting movement that the instrument allows.

The range of positions and of curvatures obtainable from the spatula-blade 3, with respect to the handle 2, is, in any case, of an extent large enough to make the use of the instrument effective under any conditions in which mechanical, muscular or articular difficulties, in the patient's head, mouth or neck are encountered.

Such efficiency during use allows, when using the instrument according to the invention, to introduce an intubation cannula 40 for connection to respiratory equipment for equivalent medical purposes, not shown in the drawings, by making the cannula travel along a guide which follows a path 42 determined by an area, substantially an L, formed by the group of elements 10, 11,12 with respect to the position of the blade sections 30,31,32, allowing the possibility of guiding the cannula up to the point of arrival, through the larynx, the trachea to the lungs by means of the illumination means 13 or of LEDs, or to carry out an exploration by employing image transmission systems carried by an optical fiber system or, alternatively, by employing the possibilities afforded by a laser sheaf.

What is claimed is:

1. A pivoting laryngoscope having a power-driven spatula for performing intubation in patients, comprising:

a handle for gripping the laryngoscope;

a curved spatula blade having one end connected to said handle, and being subdivided into a plurality of adjacent, sequentially arranged sections, at least two of said sections being pivotally connected together at a fulcrum;

motorization means located within said handle and being activatable for generating a movement; and motion transmission means operatively connecting said motorization means to at least one of said sections for transmitting the movement of said motorization means to said at least one section, whereby said at least one section is moved relative to the fulcrum and within a predetermined arc, thereby changing a curvature of said curved spatula blade.

2. The pivoting laryngoscope defined in claim 1, wherein said motorization means comprises:

power means operatively connected to said at least one section via said motion transmission means for generating the movement to move said at least one section;

power feeding means electrically connected to said power means for feeding said power means with power; and operating means electrically connected to said power means and said power feeding means for activating said power means.

3. The pivoting laryngoscope defined in claim 1, wherein one of said sections forms an end of said curved spatula blade, said one section having a free, terminal end with a circular cross-section.

4. The pivoting laryngoscope defined in claim 1, wherein said curved spatula blade is flattened.

5. The pivoting laryngoscope defined in claim 1, wherein said handle has a longitudinal central axis and is hollow, said handle including a superior end having said curved spatula blade attached thereto, a central portion adjacent to the superior end and having a rectangular cross-section viewed perpendicular to the axis, said central portion being narrow relative to the superior end for the gripping of the laryngoscope, said handle further having an inferior end adjacent to the central portion and being symmetrical to the superior end.

6. The pivoting laryngoscope defined in claim 2, wherein said power means comprises an electric motor, and said power feeding means comprises at least one rechargeable battery for feeding said electric motor with a direct current.

7. The pivoting laryngoscope defined in claim 2, wherein said power means comprises an electric motor, said operating means activating said electric motor to generate the movement to move said at least one section via said motion transmission means.

8. The pivoting laryngoscope defined in claim 1, wherein said at least two sections comprise a first and second section pivotally connected together at a first pivot point, and wherein said plurality of sections includes a third section pivotally connected to the second section at a second pivot point, said sections being individually rotatable about their respective pivot points, whereby a progressive rotation of said sections adjustably and reversibly changes the curvature of said curved spatula blade within the predetermined arc.

9. The pivoting laryngoscope defined in claim 1, wherein said motion transmission means comprises:

a rotatable transmission shaft having a first end connected to said motorization means, and a second, threaded end;

a tubular tang having a threaded hole receiving said threaded end; and a plurality of transmission elements connecting said tubular tang with said curved spatula blade, wherein rotation of said transmission shaft by said motorization means causes said tubular tang to move along a stroke path, thereby moving said transmission elements and said curved spatula blade.

10. The pivoting laryngoscope defined in claim 9, wherein said transmission elements comprise a pivotable elbow plate having a first end hinged to said tubular tang, a first extension shaft having a first end hinged to a second end of said elbow plate, and a second extension shaft having a first end hinged to a second end of said first extension shaft, said second extension shaft having a second end hinged to one of said sections of said curved spatula blade; wherein moving said tubular tang along the stroke path causes said elbow plate to pivot, thereby causing said first extension shaft to move in a linear direction, and causing said at least one section to move within the predetermined arc.

11. The pivoting laryngoscope defined in claim 1, wherein one of said pivotally connected sections comprises a first semi-circular plate integrally formed therewith, said first plate having a radial ring-shaped groove formed therein, and wherein the other of said pivotally connected sections comprises a second semi-circular plate integrally formed therewith, said second plate having a radial ring-shaped ledge formed thereon and projecting into the ring-shaped groove to pivotally connect said sections together.

12. The pivoting laryngoscope defined in claim 11, wherein said plurality of sections includes at least three sections pivotally connected together, each pair of adjacent sections being pivotally connected together using a respective first semi-circular plate and a second semi-circular plate.

13. The pivoting laryngoscope defined in claim 1, wherein one of said sections forms an end of said curved spatula blade, said one section having a performing element formed thereon, said performing element having a free, terminal end; further comprising an illuminating device located on said terminal end.

14. The pivoting laryngoscope defined in claim 13, wherein said terminal end has an opening therein for accommodating an optical fiber system or a laser sheaf.

15. The pivoting laryngoscope defined in claim 13, further comprising a rechargeable battery located in said handle and being electrically connected to said illuminating device, and a switch located in said handle and being electrically connected to said battery and to said illuminating device.

16. The pivoting laryngoscope defined in claim 13, wherein said illuminating device comprises a luminous diode or an LED.

17. The pivoting laryngoscope defined in claim 1, further comprising a housing attached to said handle for accommodating a connection plug; wherein one of said sections forms an end of said curved spatula blade, said one section having a performing element formed thereon, said performing element having a free, terminal end with an opening therein, and wherein said curved spatula blade includes a channel extending along a length of said blade from said housing to the opening for accommodating a semiconductor laser sheaf attached to the connection plug.

18. The pivoting laryngoscope defined in claim 1, wherein each of said sections has an essentially L-shaped cross section as viewed along a length of said spatula blade, with a base of the L-shape being greater than a height of the L-shape, said L-shaped sections collectively forming a guide path along which a cannula is guidable.

19. The pivoting laryngoscope defined in claim 18, wherein one of said sections forms an end of said curved spatula blade; further comprising an illuminating device located on a terminal end of said one section, said illuminating device being illuminated during the guiding of the cannula.

* * * * *